United States Patent [19]

Stern

[11] 4,438,138

[45] Mar. 20, 1984

[54] REDUCTION OF CHOLESTEROL WITH META-CHLORO α-T-BUTYLAMINOPROPIOPHENONE

[75] Inventor: Warren C. Stern, Raleigh, N.C.

[73] Assignee: Burroughs Wellcome Co., Research Triangle Park, N.C.

[21] Appl. No.: 447,412

[22] Filed: Dec. 6, 1982

[51] Int. Cl.³ .......................................... A61K 31/135
[52] U.S. Cl. .................................... 424/330; 564/345
[58] Field of Search ......................................... 424/330

[56] References Cited
PUBLICATIONS

*Chemical Abstracts,* 98: 172306u (1983) [Maxwell, R., et al., *Pharmacol. Biochem. Prop. Drug Subst.* 1981, 3, 1–55].

*Primary Examiner*—Richard A. Schwartz

*Attorney, Agent, or Firm*—Donald Brown

[57] ABSTRACT

A method of treatment for reducing cholesterol in humans by the administration of the compound of the formula I

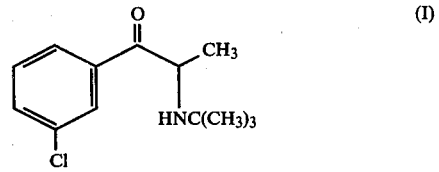

or a pharmaceutically acceptable acid addition salt thereof in a non-toxic, effective therapeutic amount (calculated as base) to a human in need thereof.

8 Claims, No Drawings

REDUCTION OF CHOLESTEROL WITH META-CHLORO α-T-BUTYLAMINOPROPIOPHENONE

BACKGROUND OF THE INVENTION

This invention is directed to a method of treatment for reducing cholesterol in a human by the administration to the human, e.g. a human having an elevated cholesterol level (i.e. above normal), of the compound of the formula I

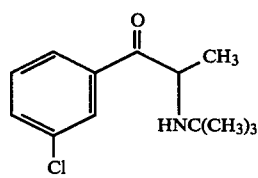

or a pharmaceutically acceptable acid addition salt thereof in a non-toxic, therapeutic amount (calculated as base) to a human in need thereof.

In U.S. Pat. Nos. 3,819,706 and 3,885,046, the compound of formula I (named m-chloro-α-t-butylaminopropiophenone) and salts thereof were disclosed as being antidepressants.

The compound of formula (I) (the active ingredient) or the pharmaceutically acceptable acid addition salt thereof is preferably administered in unit dosage form to the human being treated.

A pharmaceutical composition containing a compound of formula (I), or a pharmaceutically acceptable salt thereof, may be presented in discrete units such as tablets, capsules, ampules or suppositories, each containing an effective amount of the compound or salt.

As an example, for the treatment of humans having higher than desirable cholesterol levels the preferred unit dosage of a compound of formula (I) or an acid addition salt thereof (as the base) for oral administration, or administration as a suppositiory, is about 15 milligrams to 500 milligrams, preferably 15 milligrams to 300 milligrams, and the most preferred unit dosage is 150 milligrams to 250 milligrams per day, (t.i.d.), three times a day for a 70 kg adult. Therapeutic (effective) dosage in humans is preferably 1 to 10 mg/kg (orally) per day in order to treat a patient. Treatment is given on a continuous basis to a person who had already been identified as having higher than normal cholesterol levels. Generally humans are considered as having higher than normal cholesterol levels when such levels exceed 250 mg/100 ml of serum. All the above doses are given in terms of the weight of a compound of formula (I) in the form of its base, but as will be appreciated from the foregoing information, it may be administered in the form of a pharmaceutically acceptable acid addition salt thereof. Parenteral administration may be used and in this case the parenteral dose would be about ½ the oral dosage.

A compound of formula (I) or pharmaceutically acceptable salts thereof may be presented as an oral unit preparation (for example as a cachet, tablet or capsule) containing one or more pharmaceutically acceptable carriers which may take the form of solid diluents such as lactose, cornstarch, micronized silica gel as well as other excipients known in the art.

It should be understood that in addition to the aforementioned ingredients, the pharmaceutical composition of this invention may include one or more of additional ingredients e.g., pharmaceutically acceptable carriers such as diluents, buffers, flavouring agents, binders, surface active agents, thickeners, lubricants, preservatives, and the like. The formulations may be prepared by admixture of the ingredients, and, if necessary, shaping the resulting mass, and filling into suitable containers.

The compound used in this invention is preferably presented for use as a pharmaceutically acceptable acid addition salt. Examples of some of the pharmaceutically acceptable salts which can be utilized are salts of the following acids: hydrochloric, sulfuric, phosphoric and toluenesulphonic.

Reference should be had to U.S. Pat. Nos. 3,819,706 and 3,885,046, which are incorporated herein by reference hereto for a discription of the preparation of the compound of formula (I), acid addition salts thereof, tablets, capsules, parenteral solutions and suppositories incorporating same.

EXAMPLE I

The hydrochloride salt of formula I is administered as a tablet to a 70 kg human who has been identified by a clinician as having an elevated cholesterol. The human is orally administered a daily dose of 6 mg/kg (calculated as base) in three equally divided doses 4 to 6 hours between doses.

The human is treated continuously and then taken off the drug after cholesterol levels have reached normal levels. The human is then monitored to determine if therapy should be restarted.

EXAMPLE II

The procedure of Example 1 is followed however the hydrochloride salt at the same dosage is orally administered as an orange flavored aqueous solution, 2 teaspoons three times daily (75 mg base per spoonful).

I claim:

1. A method of reducing cholesterol levels in a human in need thereof, which comprises administering to said human an effective, non-toxic, cholesterol-lowering amount of a compound of the formula (I)

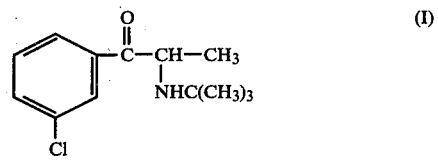

or a pharmaceutically acceptable acid addition salt thereof.

2. The method of claim 1 in which a pharmaceutically acceptable acid addition salt thereof is administered.

3. The method of claim 2 in which the salt is the hydrochloride salt.

4. The method of claim 1, 2 or 3 in which the compound or salt is administered in a pharmaceutically acceptable carrier therefor.

5. The method of claim 1, 2, or 3 in which the compound or salt is administered orally.

6. The method of claim 5 in which the compound or salt is administered in a pharmaceutically acceptable carrier therefor.

7. The method of claim 1, 2, or 3 in which the human has an initial cholesterol level greater than 250 mg/100 ml serum.

8. The method of claim 1, 2, or 3 in which the human has an above normal cholesterol level.

* * * * *